United States Patent [19]

Pile

[11] 4,228,393
[45] Oct. 14, 1980

[54] MOISTURE METER

[75] Inventor: James E. Pile, Louisville, Ky.

[73] Assignee: Brown & Williamson Tobacco Corporation, Louisville, Ky.

[21] Appl. No.: 933,226

[22] Filed: Aug. 14, 1978

[51] Int. Cl.$^3$ .............................. G01R 27/26
[52] U.S. Cl. ..................... 324/61 R; 324/61 QS; 331/65
[58] Field of Search ............ 324/61 R, 236, 237, 324/61 QS, 61 P; 331/65

[56] References Cited

U.S. PATENT DOCUMENTS

| 3,397,364 | 8/1968 | Crandall | 331/65 |
| 3,443,220 | 5/1969 | Spademan | 324/61 R |

OTHER PUBLICATIONS

Ogren, V. G., "Sensor Circuit . . . ", IBM Tech. Dis. Bull., vol. 14, No. 4, Sep. 1971, p. 1225.

Primary Examiner—Ernest F. Karlsen
Attorney, Agent, or Firm—Charles G. Lamb; William J. Mason

[57] ABSTRACT

A meter for measuring the dielectric constant of a predetermined amount of tobacco to determine the moisture content. The meter includes a sample holder with a capacitor to retain a predetermined amount of tobacco between the plates of the capacitor. A stable reference frequency, a phase comparator, and a voltage controlled oscillator are interconnected to form a phase-locked loop frequency controller. The voltage controlled oscillator is connected to the capacitor to detect a change in capacitance causing the oscillator to attempt to change frequency which in turn causes the output of the phase comparator to change and hold the circuit to the reference frequency. The phase comparator output is proportional to the moisture content of the tobacco. An indicator is responsive to the electrical output of the phase comparator to indicate the moisture content.

9 Claims, 4 Drawing Figures

MOISTURE METER

BACKGROUND OF THE INVENTION

Two common ways of measuring the moisture content of a material such as tobacco are known as the Kappa system which employs a Kappa moisture meter and the oven method.

The Kappa moisture meter measures the permittivity, or dielectric coefficient of the tobacco. This can, in turn, be correlated with moisture content. The Kappa meter uses a heterodyne circuit to process the signal. In general, the meter measures permittivity at radio frequencies. Radio frequency capacitor type moisture meters have been used by the paper, grain and tobacco industries for years. Although these meters have become more sophisticated through the years, most are still difficult to read and difficult to automatically correct for temperature variation.

The oven moisture tests are of a different nature and do not relate to the radio frequency type of process for relying on permittivity to determine moisture content. They are more difficult and time consuming to employ.

Most moisture meters presently used by the tobacco industry, for example, operate on one of three principles of measurement; dielectric constant, infrared absorption, and microwave absorption. The meter of the present invention measures the dielectric constant. The difference between this meter and others using the same principle of measurement lies in the method of detection. Ordinarily, the change in dielectric constant due to a change in sample moisture content is measured by mixing two radio frequencies (R.F.) signals in an R.F. bridge. The resulting output is the difference between the two. The detection system employed by the circuit of this invention is based on a phase-locked loop. Two oscillators are used in a manner which makes the system considerably more sensitive to changes in sample dielectric constant than previous capacitance type moisture meters.

Phase-locked loops have been used for many years. Originally they made use of vacuum tubes and were very large and complex. Therefore, aside from use as frequency controllers for high power, high frequency transmitters, they were not very practical. In recent years, with the advent of transistors, the size of the phase-locked loop has been drastically reduced. However, initially they were still complex and expensive. As the state of the art progressed from transistors to monolithic integrated circuits (IC), the phase-locked loop became smaller and less complex. Just a few years ago a phase-locked loop was developed containing essentially all of its components on one IC chip. Naturally, price and complexity, as well as physical size, decreased tremendously. Phase-locked loops are now very popular as FM and T.V. detector circuits, local oscillator control in VHF receivers and transmitters, and as frequency synthesizers.

Accordingly, improvements in radio frequency type meters are still in demand and particularly to develop and provide for increased versatility in the meter, reduction in cost and reliability.

SUMMARY OF THE INVENTION

With the above background in mind, it is among the primary objectives of the present invention to provide an improved moisture meter utilizing the principle of permittivity measurement at radio frequencies for measuring the moisture content in tobacco and other materials. The instrument is designed to measure batch samples (one at a time) or "on-line" continuous samples. The instrument differs from prior art radio frequency type meters in the method of detection of the capacitance of the sample. An integrated circuit phase-locked loop is used as a detector.

It is an object of the present invention to provide a phase-locked loop meter which offers the possibility of readily applied options of automatic temperature correction, direct display of percent moisture content, direct display of sample temperature, strip chart recorder output, computer compatible BCD output, and easily adjustable frequency of operation. Therefore, the optimum frequency for a given sample may be chosen. No known batch type meter offers the possibility of all these options.

The moisture meter of the present invention is simple in design, reliable, inexpensive and versatile due in part to the use of integrated circuits throughout. Improved precision of measurement is also an advantage of the present invention. In general the circuitry of the present invention offers good readability, ease of operation for unskilled workers and the possibility of direct moisture reading.

In summary, a meter is provided for measuring the dielectric constant of a predetermined amount of material to determine the moisture content thereof. The meter includes a sample holding means to retain a predetermined amount of material between the plates of the capacitor. A stable reference frequency means, a phase comparator, and a voltage controlled oscillator (VCO) are interconnected to form a phase-locked loop frequency controller. The voltage controlled oscillator is connected to the capacitor to detect a change in capacitance causing the oscillator to attempt to change frequency which in turn causes the output of the phase comparator to change and hold the VCO to the reference frequency. The output of the phase comparator is proportional to the moisture content of the material. Indicating means is responsive to the output of the phase comparator to indicate the moisture content.

With the above objectives among others in mind, reference is made to the attached drawings.

DETAILED DESCRIPTION

Figure 1:
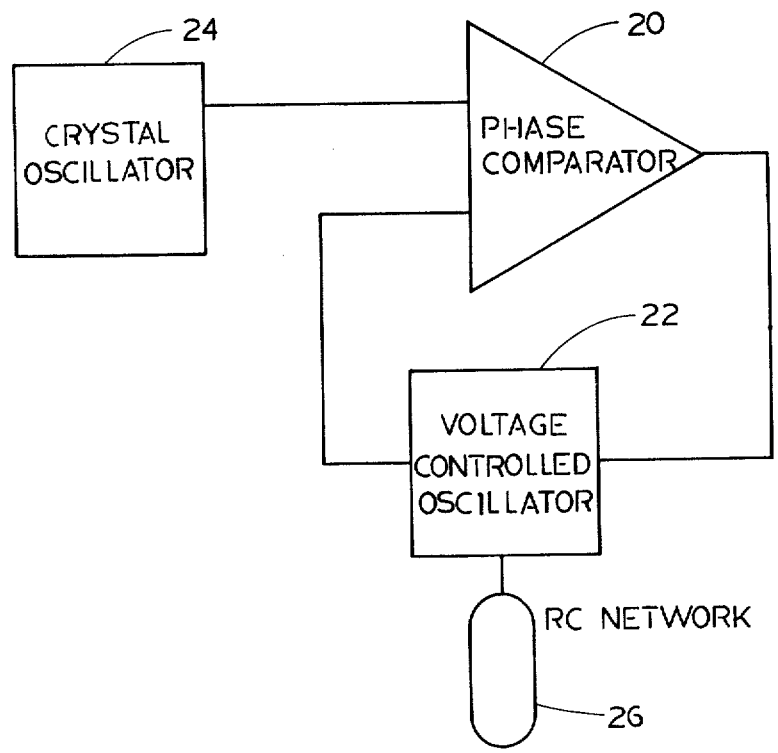
FIG. 1 is a block diagram of the phase-locked loop portion of the circuitry of the meter.

The block diagram of FIG. 1 generally shows the phase-locked loop system of the present invention. It consists of a phase comparator 20, a voltage controlled oscillator 22 and a stable reference frequency 24. The term "phase-locked loop" actually describes a condition rather than a device. The condition under which the system constitutes a phase-locked loop is that the frequency of the voltage controlled oscillator, as determined by a RC network 26, be near enough to the reference frequency that the phase comparator output forces the voltage controlled oscillator to lock onto the reference frequency. Once this lock occurs, voltage controlled oscillator 22 will remain at the reference frequency. The RC network 26 associated with voltage controlled oscillator 22 would oscillate if the voltage input to the voltage controlled oscillator 22 from the phase comparator 20 were at zero. If an attempt is made to change the voltage controlled oscillator 22 while under locked conditions, the phase comparator output will change, adjusting the voltage controlled oscillator 22 to the reference frequency. Thus, the phase-locked loop is a closed loop frequency controller.

Figure 2:
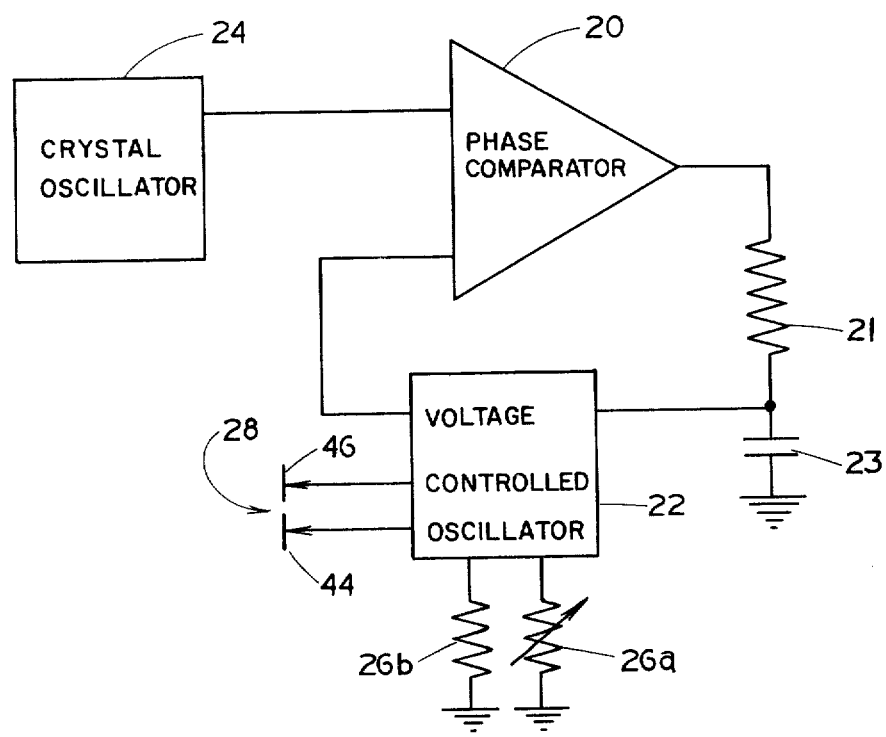
FIG. 2 is a block diagram of the circuitry of the invention.

Since the operation of a moisture meter using the dielectric constant principle is dependent on the ability to detect a change in dielectric constant, or capacitance, the phase-locked loop may be used to measure this change. The sample of material containing moisture, such as tobacco, which forms the dielectric is placed between the plates 44 and 46 of a capacitor forming part of a sample cell 28 as shown in FIG. 2. The capacitor is part of the voltage controlled oscillator RC network 26 (FIG. 1) which includes a variable resistor 26a and a fixed resistor 26b (FIG. 2). The dielectric constant of tobacco increases as the moisture increases. This causes the voltage controlled oscillator 22 to see a change in capacitance. As a result, voltage controlled oscillator 22 tries to change frequency, but the output of the phase comparator 20 changes, holding the frequency at the reference point. As the sample moisture content increases, the output of phase comparator 20 increases, wherein the high frequency component present in the output of comparator 20 is removed by a filter composed of resistor 21 and capacitor 23. The filter output is then applied to the controlled input of the oscillator 22. The operation of this system occurs in micro seconds; therefore, no significant frequency change ever takes place.

The moisture measuring circuit, which operates at a constant frequency, produces an electrical output which is the analog of sample moisture content. This output may be used to operate a meter, a recorder, or any voltage driven indicating device.

Figure 3:
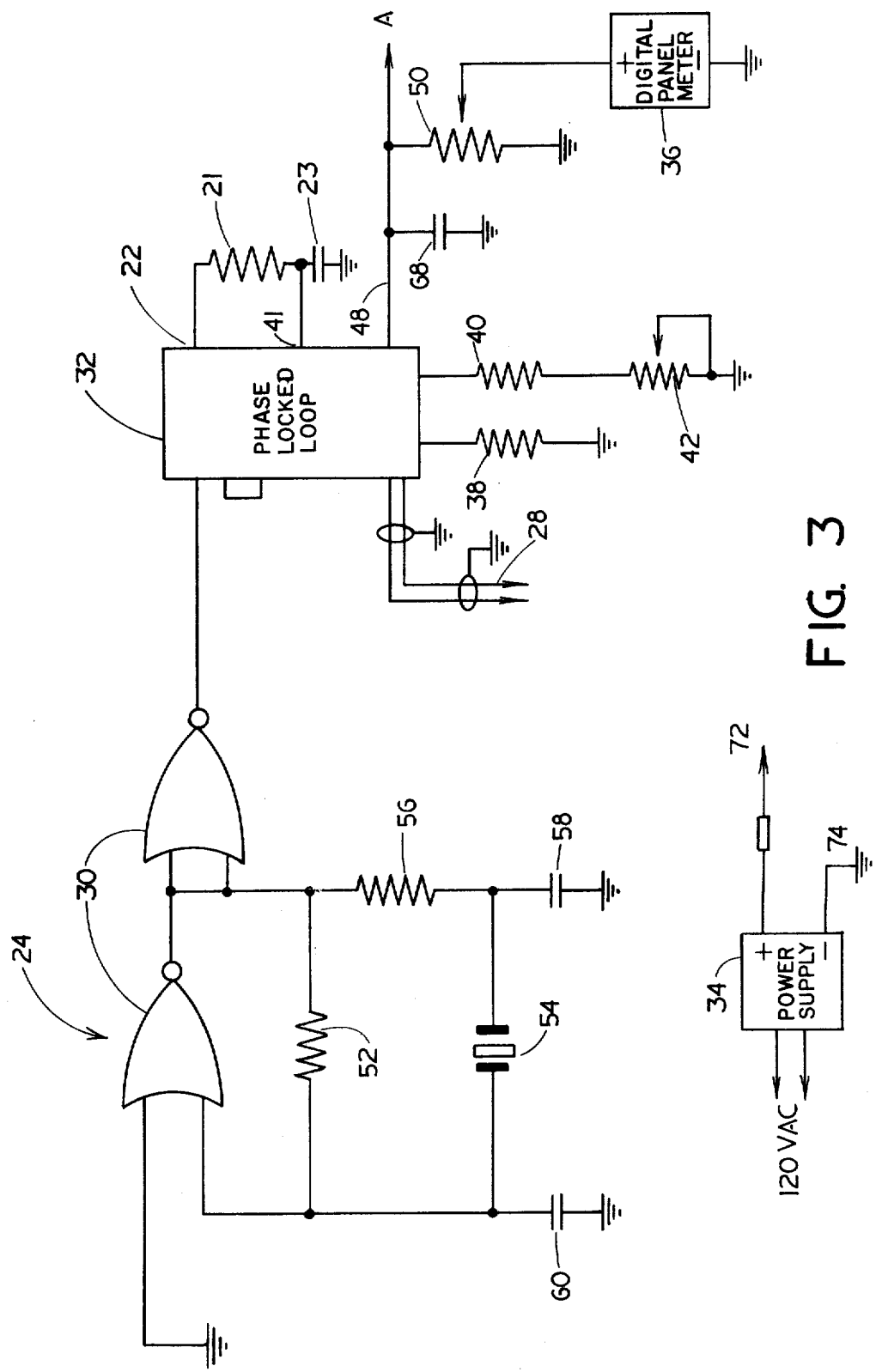
FIG. 3 is a schematic view of the circuitry of the invention.

FIG. 3 depicts the schematic circuitry of the present invention. Two standard components within the circuitry are MC 14001 quad nor gates 30 and MC 14046 phase-locked loop 32, both standard integrated circuits. A 15 volt power supply 34 is employed to supply power to the integrated circuits 30 and 32, but any 12–15 volt well-regulated supply could be used. A digital panel meter 36 is provided to read the output of the phase-locked loop 32, meter 36 being 3½ digits. It is realized that any meter with a display of 3½ to 4½ digits may be used. The voltage range of the meter 36 should be 0–200 mv. Furthermore, an analog meter of the same range may be used.

The MC 14001 100 KH2 crystal oscillator 24 has sufficient power to drive the phase comparator 20 of the MC 14046 phase-locked loop and it has been found that an output of 12–14 volts is generally sufficient. The output of the phase comparator 20 is generally filtered and input into the control line of the voltage controlled oscillator 22, it being realized that the filtering required is not critical. The values used here provide a cut-off frequency of about 1.6 Kc. A higher cut-off can cause some jitter in the output. A lower cut-off will cause the loop to operate a bit slowly.

The free run frequency of the oscillator 22 is determined by the resistors 38 and 40 of the phase-locked loop 32. Resistor 40, having a resistance 47K, in series with a zero control 42, a 10-turn potentiometer prevents the frequency of the oscillator 22 from exceeding a predetermined value. The sample receptacle 28 consisting of two parallel plates 44 and 46 spaced far enough apart to accept a standard size cell (not shown) is also provided, as discussed hereinbefore.

An output pin 48 from a buffer amplifier internal to the phase-locked loop 32 is provided. The input of the buffer amplifier is tied internally to the voltage controlled oscillator control input as designated by numeral 41. This provides more drive available at this point than at the output of the phase comparator 20. Also, changes in the output circuit conditions do not affect the phase-locked loop operation. A span control 50 is connected to the pin 48, and like the zero control 42, is a 10-turn potentiometer.

Other components are provided in the circuit to assist in proper oscillation of the oscillator 24 and include 22 M resistors 52, 100 KC crystal 54, 22K resistor 56, 20 PF capacitor 58 and 20 PF capacitor 60. A capacitor 68 having a 0.1 MF value is provided to eliminate the high frequency component from the loop 32.

Also for circuit description purposes, it should be pointed out that lead 72 and ground 74 go to appropriate pins (not shown) of nor gates 30 and appropriate pins (not shown) of phase-locked loop 32, it being realized that lead 72 and ground 74 do not go to the same pins.

In summary, a phase-locked loop consists of a voltage control led oscillator, and a phase comparator. The frequency of the voltage controlled oscillator is determined by an RC network consisting of two resistors and one capacitor. The frequency, as calculated for the values used, determine the "free run frequency" i.e. the frequency at which the voltage controlled oscillator runs with no external influences. The output of the voltage controlled oscillator is input into the phase comparator. The other phase comparator input is derived from a stable source of reference frequency, in this case, a crystal controlled oscillator or frequency synthesizer. The phase comparator output is proportional to the phase difference between the two signals. This output is filtered and used as the control input to the voltage controlled oscillator. As the phase comparator output rises, the voltage controlled oscillator frequency is automatically adjusted until the voltage controlled oscillator frequency is equal to the reference frequency. At this point, there is no significant difference in phase. The phase-locked loop moisture meter operates exactly as the above description, but the proper probe assembly is substituted for the fixed capacitor in the RC network. Therefore, the probe and sample become the capacitance controlling the free run frequency. As the moisture content increases, the free run frequency tends to lower. However, since this system is in a locked condition, the phase comparator output rises causing the voltage controlled oscillator to almost instantaneously adjust itself to the reference value. Since the phase comparator output is proportional to the phase difference, and since the phase difference is caused by a change, or attempted change in frequency, the phase comparative output is proportional to the sample capacitance which is proportional to the moisture content of the sample.

The frequency used may be from a few cycles per second up to about 2 mHz. The most useful range appears to be between 100 kHz and 1.0 mHz. If a frequency synthesizer is used as reference, the frequency may be readily changed to suit the probe and material under test. For purposes of the depicted and described embodiment, a reference frequency of 100 kHz is employed for crystal oscillator 24.

Figure 4:
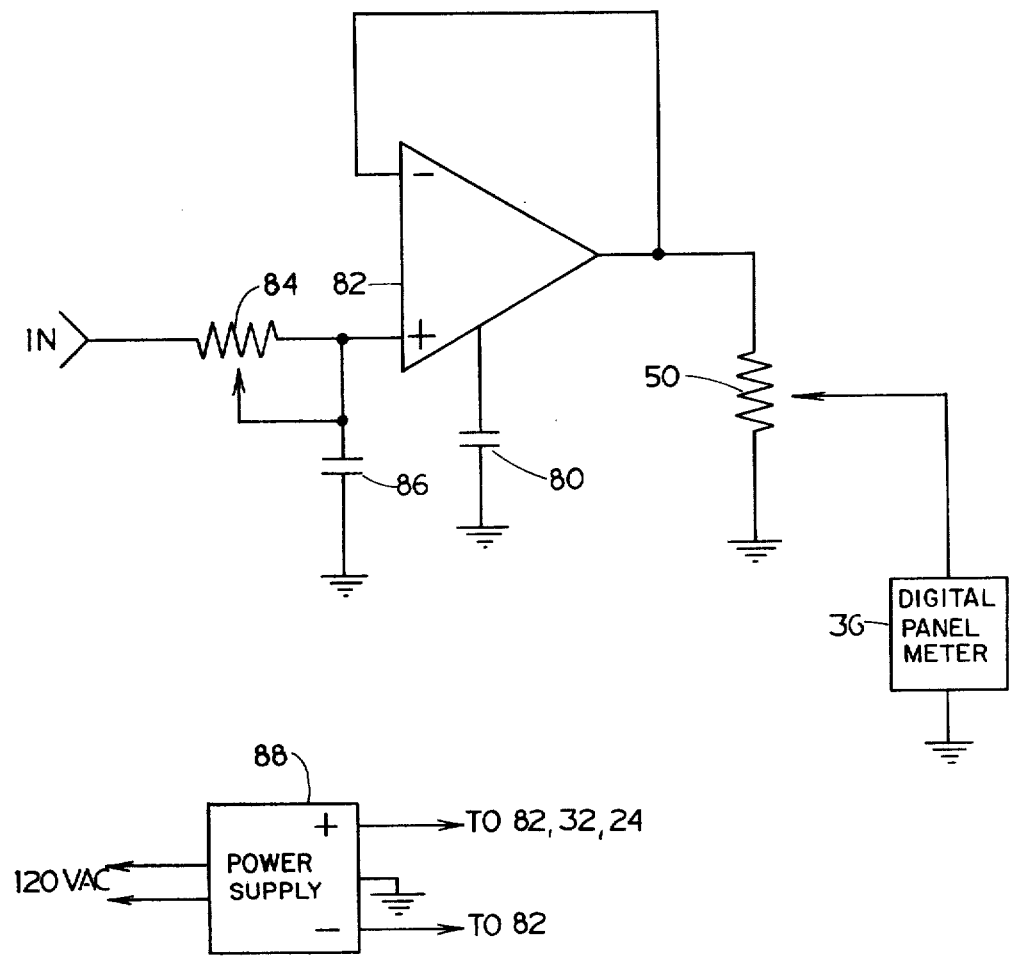
FIG. 4 is a schematic view of the circuitry of the invention when used in a continuous operation.

It is also realized that the moisture meter may be used continuously as well as batchwise as discussed previously. When used as an on-line, or continuous meter, it is desirable to provide signal damping to prevent the meter from following short term variations of moisture. FIG. 4 being a circuit designed to accomplish this damping. In FIG. 4, the input of the damping circuit is taken from point A of FIG. 3. Resistor 50 and meter 36 in FIG. 3 are moved to the final output stage as shown in FIG. 4.

FIG. 4 is an operational amplifier connected as a buffer with very high input impedance. The gain is unity. Incorporated within the circuit is a compensating capacitor 80 which prevents instability in an amplifier 82. A circuit time constant which includes variable resistor 84 and capacitor 86 is provided to filter the signal from the phase-locked loop 32 (FIG. 3). An increase in input voltage will cause an increase in output voltage which is totally dependent on the time constant of the resistor 84 and capacitor 86. Therefore, short-term signals are effectively averaged.

When using the moisture meter of the present invention as a continuous device, the circuit of FIG. 4 requires that the power supply (numeral 34 of FIG. 3) be replaced with a dual voltage supply 88 in order to operate the amplifier 82 and the sample plates 44 and 46 are disposed as a fringing capacitor and are located either above or below the continuous flow of material.

Thus the several aforenoted objects and advantages are most effectively attained. Although several somewhat preferred embodiments have been disclosed and described in detail herein, it should be understood that this invention is in no sense limited thereby and its scope is to be determined by that of the appended claims.

I claim:

1. A meter for measuring the dielectric constant of a predetermined amount of material constituting a sample to determine the moisture content thereof comprising:
   a capacitor having means to receive the sample, a stable reference frequency means, a phase comparator, and a voltage controlled oscillator interconnected to form a phase-locked loop frequency controller;
   the voltage controlled oscillator being connected to the capacitor to detect a change in capacitance causing the voltage controlled oscillator to change frequency which due to the phase-locked loop condition causes the ouput of the phase comparator to change and maintain the frequency of the voltage controlled oscillator at the frequency of the stable reference frequency means;
   the phase comparator output being proportional to the moisture content of the material; and,
   indicating means connected to the phase comparator and responsive to the output of the phase comparator to indicate the moisture content.

2. The meter in accordance with claim 1 wherein the predetermined amount of material is tobacco.

3. The meter in accordance with claim 1 wherein the phase-locked loop condition is produced by means for determining the frequency of the voltage control oscillator near enough to the reference frequency that the phase comparator output forces the voltage controlled oscillator to lock onto the reference frequency thus causing the voltage controlled oscillator to remain at the reference frequency, the means for determining the frequency of the voltage controlled oscillator being designed to control the voltage controlled oscillator if the voltage input to the voltage controlled oscillator from the phase comparator is at a preselected point above zero thereby producing locked conditions whereby an attempt to change the voltage controlled oscillator will change the output of the phase comparator and maintain the voltage controlled oscillator at the reference frequency.

4. The meter in accordance with claim 3 wherein the capacitor is part of the means to determine the frequency of the voltage controlled oscillator.

5. The meter in accordance with claim 4 wherein the means for determining the frequency of the voltage controlled oscillator is a resistor and capacitor network.

6. The meter in accordance with claim 1 wherein the capacitor is a sample holding means to retain a predetermined amount of material.

7. The meter in accordance with claim 6 wherein the capacitor has a pair of spaced plates to receive a sample therebetween.

8. The meter in accordance with claim 1 wherein the capacitor is a fringing capacitor disposed above the flow of material.

9. The meter in accordance with claim 1 wherein the capacitor is a fringing capacitor disposed beneath the flow of material thereabove.

* * * * *